United States Patent
Graves et al.

(10) Patent No.: US 7,507,206 B2
(45) Date of Patent: Mar. 24, 2009

(54) STRESS REDUCER

(76) Inventors: Sandra L. Graves, 313 W. Madison St., LaGrange, KY (US) 40031; Margaret R. Favata, 313 W. Madison St., LaGrange, KY (US) 40031

( * ) Notice: Subject to any disclaimer, the term of this patent is extended or adjusted under 35 U.S.C. 154(b) by 325 days.

(21) Appl. No.: 10/930,811

(22) Filed: Sep. 1, 2004

(65) Prior Publication Data
US 2006/0047179 A1    Mar. 2, 2006

(51) Int. Cl.
*A61B 5/00* (2006.01)
*A61M 21/00* (2006.01)

(52) U.S. Cl. .................... 600/481; 600/26; 600/300; 600/500

(58) Field of Classification Search .................. None
See application file for complete search history.

(56) References Cited

U.S. PATENT DOCUMENTS

| | | | | |
|---|---|---|---|---|
| 3,822,693 A * | 7/1974 | King | ............................ | 600/27 |
| 4,315,502 A * | 2/1982 | Gorges | ........................ | 600/27 |
| 5,135,468 A * | 8/1992 | Meissner | ..................... | 600/28 |
| 5,304,112 A * | 4/1994 | Mrklas et al. | ................. | 600/27 |
| 5,577,990 A * | 11/1996 | Widjaja et al. | ................ | 600/27 |
| 2004/0254501 A1 * | 12/2004 | Mault | ........................ | 600/587 |

* cited by examiner

*Primary Examiner*—Robert L Nasser
(74) *Attorney, Agent, or Firm*—Hasse & Nesbitt LLC; Ronald J. Richter

(57) ABSTRACT

The present invention combines into a single housing a multiplicity of features that may be used separately or together to facilitate stress reduction in the user. A central computer receives inputs and sends signals to facilitate activation of a visual display as well as an audio output. Several power supply options are provided. A pulse sensor may be attached to the user to sense their pulse rate. The audio input provides a soothing noise such as a beating sound, the frequency of which may be adjusted, for example, 30 to 120 beats per minute. A voice synthesizer may speak directions to the user such as, for example, instructing the user to breathe in and out at a certain rate. A timer and speed control permit ready adjustment of the frequency of beats as well as the frequency during which voice synthesizer messages are provided. A microphone and tape recorder allow the user to tape record their own stress reducing instructions. A visual display includes an arc made up of a multiplicity of LEDs and a display of the heart rate. The audio output may include a speaker and a volume control.

20 Claims, 3 Drawing Sheets

STRESS REDUCER

BACKGROUND OF THE INVENTION

The present invention relates to a stress reducer. All of nature has a rhythm, from the contractions of birth to the ebb and flow of the tide. People interact and react to all of the rhythms around us. The examples include the healthy beat of the heart, the number of eye movements during dream sleep, the principles of isomorphism and homeostasis—meaning that we interact and react to all of the rhythms around us. At an extremely primitive level, we experience and sense the difference between when we are "in synch" or "out of synch."

There is a human quest for balance in life's rhythms. When life's rhythms become imbalanced for a significant period of time, human stress becomes greater and the quality of life is reduced. If it were possible to devise a way to easily facilitate stress reduction in a human being, a person's quality of life would be significantly enhanced. It is with these thoughts in mind that the present invention was developed.

SUMMARY OF THE INVENTION

The present invention relates to a stress reducer. The present invention includes the following interrelated objects, aspects and features:

(1) The present invention is intended to combine into a single a housing a multiplicity of features that may be used separately or together to facilitate stress reduction in the user.

(2) The inventive device has a central controller or computer that receives inputs and sends signals responsive to input commands or receipt of signals from sensors to facilitate activation of a visual display as well as an audio output. Several power supply options are provided including battery power, alternating current via a transformer, or a cigarette lighter adapter.

(3) A pulse sensor may be attached to the user, for example, attached to the user's finger or wrist, to sense the pulse rate of the user and provide that information to the computer via an electrical conductor. Additionally, the audio input may be used to provide a soothing noise such as, for example, a beating sound similar to that of a metronome, the frequency of which may be adjusted within a desired range such as, for example, 30 to 120 beats per minute. The audio output may also be employed to permit the user to selectively hear a human voice created by a voice synthesizer speaking directions to the user such as, for example, instructing the user alternately to breathe in and breathe out at a certain rate of breaths per unit time.

(4) A timer and speed control are incorporated into the device to permit ready adjustment of the frequency of beats of the metronome as well as the frequency during which voice synthesizer messages are provided through the audio portion. Also, this aspect may be employed to preset a time sequence of outputs.

(5) The inventive device is also provided with a microphone and tape recorder allowing the user to tape record their own stress reducing instructions such as, for example, statements that may be periodically played instructing the user to "be calm." Additionally, the inventive device has a visual display which may include an arc made up of a multiplicity of light emitting diodes (LEDs) incorporated into a circuit allowing sequential ones of the LEDs to sequentially light and extinguish to provide an arc that the user's eyes may follow. The visual display may also include an intensity control that permits adjustment of the intensity of the display. The display may also include a display of the heart rate in beats per minute and a display of preset time sequences of outputs.

(6) The audio output device may include a speaker and a volume control therefor to allow adjustment of the intensity of sound emanating from the speaker. The timer circuit may also be used to permit programming the device to activate its functions in a sequence, i.e., for a preset period of time, thereafter deactivate for a preset period of time, thereafter reactivate for a preset period of time, and so on. A repeat button may be depressed to cause the sequence to repeat itself.

As such, it is a first object of the present invention to provide a stress reducer.

It is a further object of the present invention to provide such a device in which a number of components are combined together into a single housing to facilitate reducing the stress of the user.

It is a still further object of the present invention to provide such a device which includes audio and visual outputs as well as sensing inputs including means for sensing the pulse rate of the user.

It is a still further object of the present invention to provide such a device in which a voice synthesizer is employed to speak commands to the user when activated.

It is a yet further object of the present invention to provide such a device including the use of a microphone and tape recorder to permit the user to record and thereafter play back commands and instructions that facilitate stress reduction.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
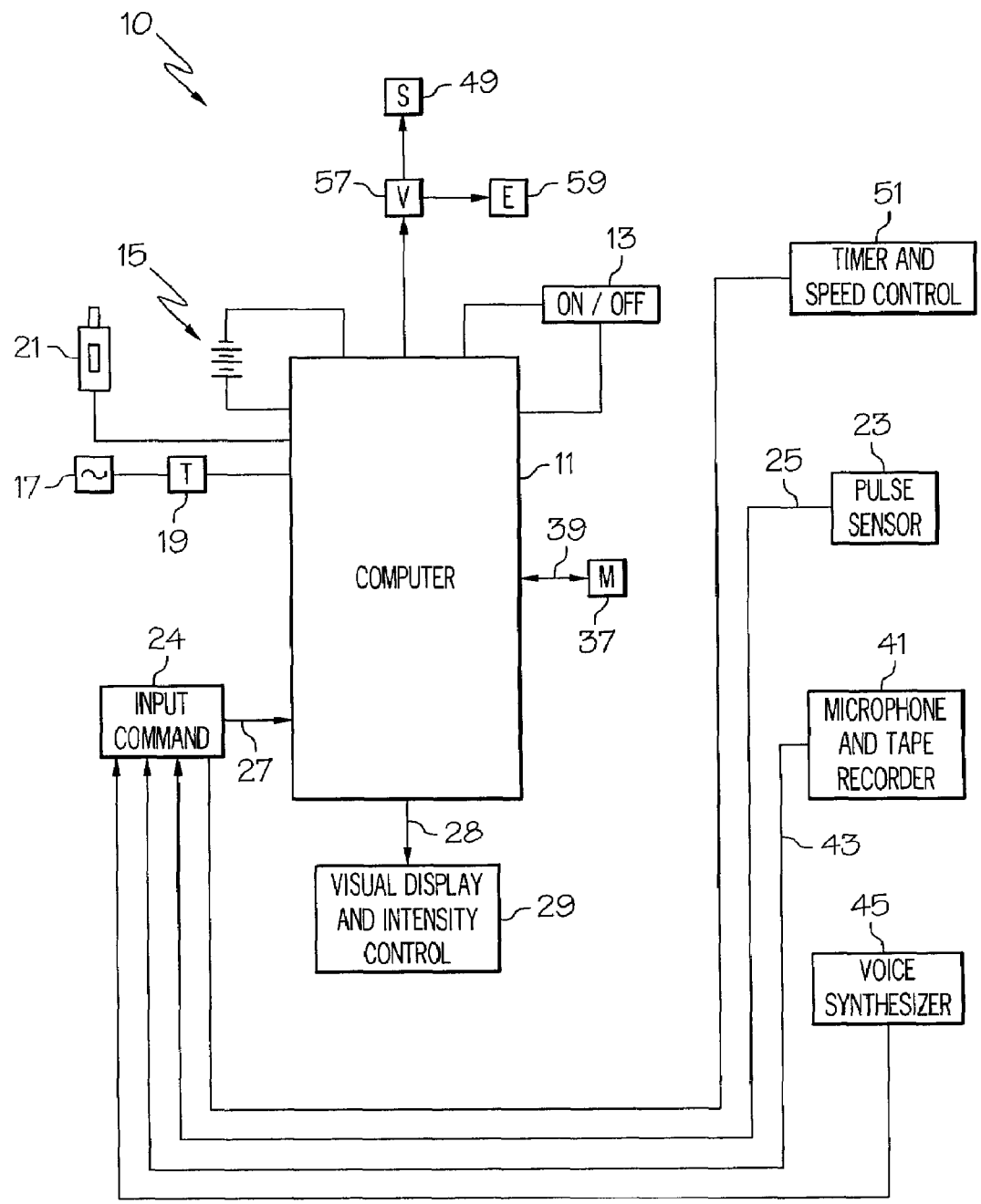
FIG. 1 shows a schematic representation of the circuitry of the present invention.

With reference, first, to FIG. 1, the present invention is generally designated by the reference numeral 10 and is seen to include a computer 11 including an on-off switch 13 permitting the computer 11 to be activated and deactivated. In the preferred embodiment, three alternative power sources are shown, including batteries 15, a source of alternating current 17 interconnected with the computer 11 via a transformer 19 that transforms alternating current into direct current power of a desired voltage, or a cigarette lighter adapter 21 that permits the inventive device 10 to be activated when in the user's vehicle. As is well known to those of ordinary skill in the art, the computer 11 may be provided with a switching mechanism to facilitate sensing which power source is being used, and connecting that power source to supply power to the computer 11 when the on-off switch 13 is closed to the on position.

With further reference to FIG. 1, the inventive device includes a pulse sensor 23 that may be attached to the user, for example, to the user's finger or wrist, to sense the rate of the user's pulse caused by the beating of the user's heart. Electrical signals generated responsive to sensing the pulse rate are sent to an input device 24, that may, for example, comprise a multiplexer or a terminal block, via a conductor 25. The input device 24 provides the signals to the computer 11 via a multi-wire conductor 27 that is designed to transmit inputs and commands to the computer from a variety of sources as will be described in greater detail hereinafter. The pulse rate is displayed on the visual display 29, particularly the display portion 31 shown in FIG. 3. The display of pulse rate may be viewed by the user. As stress is reduced, the pulse rate will inevitably reduce. Viewing this reduction contributes to stress reduction.

In a manner understood by those of ordinary skill in the art, when the computer 11 receives signals from the pulse sensor 23, the computer may selectively cause a display corresponding to the pulse rate to be displayed on the visual display 29 connected to the computer 11 via conductor 28. The visual display may include an LCD or LED readout that permits display of a numeral or numerals corresponding to the pulse rate. The visual display also includes, in the preferred embodiment, an arc-shaped line of LEDs that may be operated in a sequence corresponding to the frequency of the user's pulse.

Figure 2:
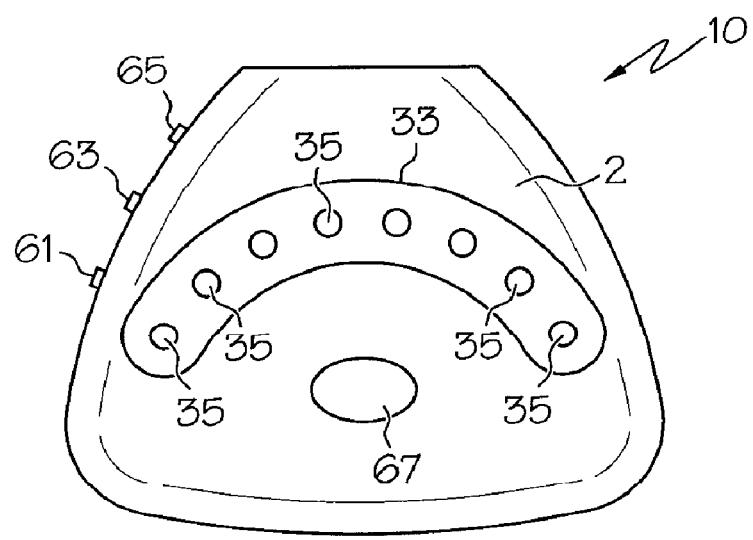
FIG. 2 shows a front view of a preferred embodiment of the housing of the present invention.
Figure 3:
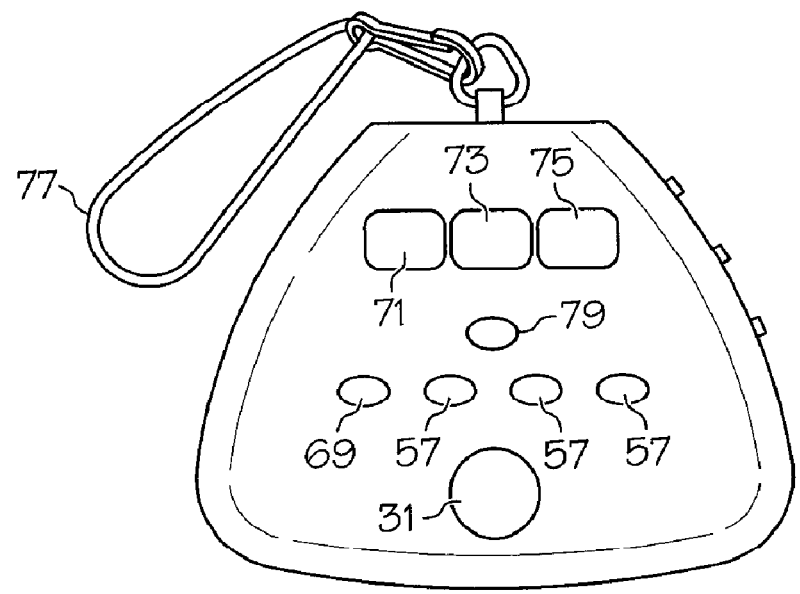
FIG. 3 shows a rear view of the housing of FIG. 1.

With reference to FIG. 3, the portion of the display that allows display of a numeral is identified by the reference numeral 31 and the aspect of the visual display that includes an arc-shaped line of LEDs is shown in FIGS. 2 and 3 and identified by the reference numeral 33. Each LED is designated by the reference numeral 35.

The computer 11 is provided with a memory section 37 that communicates back and forth with the computer 11 via a conductor 39 as seen in FIG. 1. The inventive device is also provided with a microphone and tape recorder schematically represented in FIG. 1 by the reference numeral 41. Using the microphone and tape recorder, the user can create his or her own vocal instructions that are conveyed to the computer 11 via the conductor 43, the input device 24, and the conductor 27, whereupon those instructions are stored in the memory 37 for play back as desired by the user. The instructions may be, for example, the words "calm down" or "relax" spoken in the user's voice. Additionally, a voice synthesizer 45 is provided that allows voice synthesized words to be spoken by the device 10 to the user when prompted by the user. For example, the voice synthesizer 45 may be preprogrammed with the words "breathe in" and "breathe out" which are alternately heard via the speaker 49 (FIG. 1) or earphones 59. The timer and speed control 51 (FIG. 1) is settable by the user to control the frequency of different displays. For example, the timer and speed control 51 may be adjusted to adjust the frequency in which the commands "breathe in" and "breathe out" are played from the voice synthesizer 45 through the speaker 49. For example, the words "breathe in" may be played every 12 seconds, 5 times a minute, with the words "breathe out" played between each play of the words "breathe in." The voice synthesizer is useful in regulating and slowing the breathing cycle to calm the patient.

As also seen in FIG. 1, a volume control 57 is interposed between the computer 11 and the speaker 49 to adjust the volume of the programming that is heard from the speaker 49. In the same way, earphones 59 are also connected to the computer 11 via the volume control 57 so that the volume of sounds played on the earphones 59 may also be selectively controlled.

A further function of the timer and speed control is to facilitate creation of a timing sequence of commands being given by the device 10. Thus, for example, the timer and speed control 51 may be used to first adjust the frequency by which commands are given. Thus, for example, it may be desired to cause the voice synthesizer 45 to provide signals to the speaker 49 or earphones 59 via the computer 11 and volume control 57 instructing the user to breathe every six seconds. Through the timer portion of the timer and speed control 51, the inventive device 10 may be set so that, for example, breathe commands from the voice synthesizer 45 are given every six seconds for a period of one minute, whereupon the device 10 pauses for 20 seconds during which no commands are given, whereupon for the next 60 second period breathe commands are again given—every 6 seconds. Timer and frequency control mechanisms are known per se but not in a stress reduction device in the manner contemplated by Applicants.

In the same way, commands recorded by the microphone and tape recorder 41 that have been stored in the memory 37 may be played through the speaker 49 or earphones 59 in a desired sequence and timing.

The timer and speed control 51 also includes means for providing the speaker 49 or earphones 59 via the computer 11 a sound resembling that of a metronome. The speed control may control the frequency of "beats" of the metronome sound in any desired range of frequencies such as, for example, from 30 to 120 beats per minute. Applicants have found that different ranges of frequencies of the metronome sound have differing effects on the user. Generally speaking, to relax the user, the frequency is set at a rate not to exceed 60 beats per minute. Frequencies above 60 beats per minute have been found to facilitate lifting of depression and increasing the user's heart rate.

With reference to FIGS. 1 and 2, in particular, the timer and speed control 51 may also be used to adjust the frequency of flashes of the LEDs 35 in the arc thereof designated by the reference numeral 33 and best seen in FIG. 2. Thus, the inventive device 10 can be preset so that the LEDs 35 flash sequentially from left to right or vice-versa with each LED flashing in a sequence, for example, one second after the previous LED. In this way, a pattern of flashes may be followed back and forth by the eyes of the user to soothe the user and reduce stress.

Figure 4:
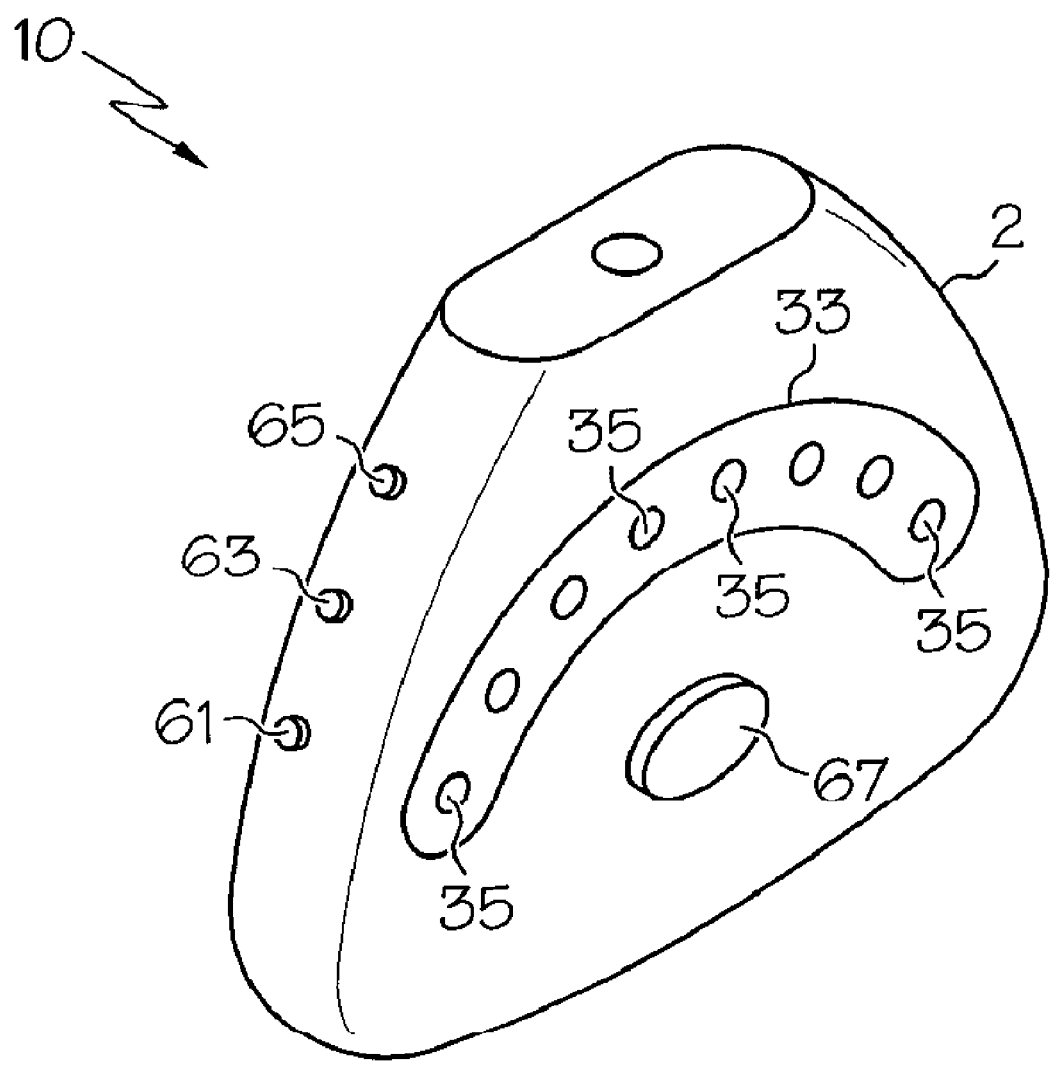
FIG. 4 shows a front left-side perspective view of the embodiment of FIGS. 2 and 3.

FIG. 4 shows, in particular, a receptacle 61 designed to receive an earphone jack from the earphone 59. The receptacle 63 shown in FIG. 4 is designed to receive an input jack from the pulse sensor 23. The receptacle 65 may be used to connect to a source of alternating current 17. The transformer 19 may be built into the housing 2 of the inventive device 10.

As explained above, the timer and speed control 51 may be employed to program into the computer 11 a sequence of operations of different features of the inventive device, for example, 60 seconds on, 20 seconds off, 60 seconds on, etc. As shown in FIG. 2, a repeat button 67 may be provided so that it may be pushed or depressed by the user to repeat a sequence that was just completed. Such a sequence is stored in the memory 37 in a manner well known to those of ordinary skill in the art, and depressing the repeat button 67 causes the sequence to be repeated for the user.

FIG. 3 shows the volume control 57 for the speaker 49 with the volume control 57 also including an on-off switch (if desired). FIG. 3 also shows a knob 69 that is intended to schematically represent the timer and speed control 51 and permits performing the functions described hereinabove with respect thereto. Additionally, FIG. 3 shows a further aspect of the visual display 29 consisting of three LCD displays 71, 73 and 75 provided to display a preprogrammed sequence of operation of the inventive device such as the 60 seconds on, 20 seconds off, 60 seconds on sequence explained above. FIG. 3 also shows a convenient carrying strap 77 that may be provided for the inventive device. As clearly seen from FIGS. 2-4, the inventive device 10 is of a size rendering it easily portable.

Additionally, FIG. 3 shows a further control 79 that may provide additional volume control for various outputs of the device. However, in the preferred embodiment, the volume control 57 may be used to control the volume of all outputs that are provided by the device.

In FIG. 3, reference numeral 79 also corresponds to the on-off switch 13 shown in FIG. 1.

Applicants have found that the inventive device is useful for people who are suffering from diverse types of stress including panic attacks while driving alone, those who have high stress jobs, and elderly people who sometimes become agitated at night. Others who may be helped by the inventive device include athletic coaches and players who experience performance anxiety immediately before an athletic contest. Others who benefit from the teachings of the present invention include those who have already experienced severe medical conditions such as, for example, a heart attack. It is important to find a way to relieve stress in heart attack survivors. The present invention is the ideal device for this particular purpose.

As such, an invention has been disclosed in terms of a preferred embodiment which fulfills each and every one of the objects of the present invention as set forth hereinabove, and provides a new and useful stress reducer of great novelty and utility.

Of course, various changes, modifications and alterations in the teachings of the present invention may be contemplated by those of ordinary skill in the art without departing from the intended spirit and scope thereof.

As such, it is intended that the present invention only be limited by the terms of the appended claims.

The invention claimed is:

1. A stress reducer, comprising:
   a. a portable housing containing a computer connected to a power source;
   b. a pulse sensor connected to said computer and adapted to sense pulse rate of a human heart, said pulse sensor sending signals to said computer representative of said pulse rate;
   c. a visual display on said housing and connected to said computer and displaying pulse rate responsive to receipt by said computer of said signals;
   d. an audio output device on said housing and connected to said computer to provide an audio output;
   e. a source of a periodic beating sound in said housing and connected to said computer and, when activated, resulting in periodic beating sounds to emanate from said audio output device;
   f. frequency adjustment means in said housing for adjusting frequency of said beating sound; and
   g. a timer circuit associated with said source of periodic beating sound and configured to alternate in a repeating sequence between a first "on" condition that activates said source of periodic beating sound for a first pre-set time period, and a second "off" condition that deactivates said source of periodic beating sound for a second pre-set time period.

2. The stress reducer of claim 1, wherein said pulse sensor is attachable to a human finger.

3. The stress reducer of claim 1, wherein said visual display includes a numeric display for displaying a pulse rate in beats per unit time.

4. The stress reducer of claim 1, wherein said audio output device includes a speaker.

5. The stress reducer of claim 4, wherein said audio output device further includes earphones.

6. The stress reducer of claim 5, further including a volume control interposed between said computer and said speaker and earphones.

7. The stress reducer of claim 1, wherein said periodic beating sound resembles a sound made by a metronome.

8. The stress reducer of claim 1, wherein said frequency adjustment means is adapted to adjust frequency from 30 to 120 beats per minute.

9. The stress reducer of claim 1, further wherein said visual display further includes a lighted display.

10. The stress reducer of claim 9, wherein said lighted display includes a plurality of lights.

11. A stress reducer, comprising:
    a. a portable housing containing a computer connected to a power source;
    b. a pulse sensor connected to the computer and adapted to sense the pulse rate of a human heart, the pulse sensor sending signals to the computer representative of the pulse rate;
    c. a visual display on the housing and connected to the computer, the visual display operable to display the pulse rate responsive to receipt by the computer of the pulse sensor signals, wherein the visual display comprises a lighted display including a plurality of lights, the plurality of lights comprising an arcuate line of light emitting diodes;
    d. an audio output device on the housing and connected to the computer to provide an audio output;
    e. a source of a periodic beating sound in the housing and connected to the computer and, when activated, resulting in periodic beating sounds to emanate from the audio output device;
    f. frequency adjustment means in the housing for adjusting frequency of the beating sound; and
    g. a timer circuit associated with the source of periodic beating sound and configured to alternate between a first condition that activates the source of periodic beating sound for a first pre-set time period, and a second condition that deactivates the source of periodic beating sound for a second pre-set time period.

12. The stress reducer of claim 11, including means for flashing the light emitting diodes in a desired pattern.

13. The stress reducer of claim 11, further including a voice synthesizer programmed with soothing words, said voice synthesizer connected to said computer.

14. The stress reducer of claim 13, wherein said frequency adjustment means is adapted to adjust frequency of sounding of soothing words per unit time by said audio output device.

15. The stress reducer of claim 11, further including a tape recorder and microphone connected to said computer for recording sounds, said computer including a memory for storing said sounds for subsequent replay.

16. A stress reducer, comprising:
    a. a portable housing containing a computer connected to a power source;
    b. a pulse sensor connected to said computer and adapted to sense pulse rate of a human heart, said pulse sensor sending signals to said computer representative of said pulse rate;
    c. a visual display on said housing and connected to said computer and including a numeric display displaying pulse rate responsive to receipt by said computer of said signals;
    d. a speaker on said housing and connected to said computer to provide an audio output;

e. a source of a periodic beating sound resembling sound of a metronome and located in said housing and connected to said computer and, when activated, resulting in periodic beating sounds to emanate from said audio output device f. frequency adjustment means in said housing for adjusting frequency of said beating sound between 30 and 120 beats per minute; and g. a timer circuit associated with said source of periodic beating sound and configured to alternate in a repeating sequence between a first "on" condition that activates said source of periodic beating sound for a first pre-set time period, and a second "off" condition that deactivates said source of periodic beating sound for a second pre-set time period.

17. The stress reducer of claim 16, wherein said audio output device further includes earphones.

18. The stress reducer of claim 17, further including a volume control interposed between said computer and said speaker and earphones.

19. The stress reducer of claim 16, further wherein said visual display further includes a lighted display including a plurality of lights, said plurality of lights comprising an arcuate line of light emitting diodes.

20. The stress reducer of claim 16, further including a voice synthesizer programmed with soothing words, said voice synthesizer connected to said computer, said frequency adjustment means being adapted to adjust frequency of sounding of soothing words per unit time by said audio output device.

* * * * *